(12) United States Patent
Ekechukwu

(10) Patent No.: US 6,180,413 B1
(45) Date of Patent: Jan. 30, 2001

(54) LOW LEVEL TOC MEASUREMENT METHOD

(75) Inventor: Amy A. Ekechukwu, Augusta, GA (US)

(73) Assignee: Westinghouse Savannah River Company, Aiken, SC (US)

(*) Notice: Under 35 U.S.C. 154(b), the term of this patent shall be extended for 0 days.

(21) Appl. No.: 09/352,794

(22) Filed: Jul. 13, 1999

(51) Int. Cl.[7] .................................................. G01N 33/18
(52) U.S. Cl. ............................ 436/146; 436/62; 436/133; 436/145; 436/155; 436/160; 436/161; 436/178; 422/78; 422/79; 422/80
(58) Field of Search .............................. 436/62, 133, 145, 436/146, 155, 160, 161, 177, 178, 181; 422/78, 79, 80; 73/61.52, 61.55; 210/656

(56) References Cited

U.S. PATENT DOCUMENTS

| | | | |
|---|---|---|---|
| 3,607,071 | * 9/1971 | Colonia et al. | 436/146 |
| 3,859,209 | * 1/1975 | Jahnsen et al. | 210/664 |
| 4,180,389 | * 12/1979 | Paul | 95/11 |
| 4,619,902 | 10/1986 | Bernard | 436/145 |
| 4,627,921 | * 12/1986 | Meyers et al. | 210/668 |
| 4,940,667 | * 7/1990 | Goldstein et al. | 436/157 |
| 5,039,424 | * 8/1991 | Mitarai et al. | 210/669 |
| 5,292,666 | * 3/1994 | Fabinski et al. | 436/114 |
| 5,315,885 | 5/1994 | Szinyei | 73/863.71 |
| 5,401,468 | 3/1995 | Patashnick et al. | 422/80 |
| 5,413,763 | * 5/1995 | Jeffers | 422/80 |
| 5,425,919 | 6/1995 | Inoue et al. | 422/67 |
| 5,567,388 | 10/1996 | Morita et al. | 422/80 |
| 5,574,230 | * 11/1996 | Baugh | 73/863.23 |
| 5,750,073 | 5/1998 | Godec et al. | 422/79 |
| 6,063,638 | * 5/2000 | Small et al. | 436/146 |

OTHER PUBLICATIONS

Supplies Chromatography Products Catalogue, 1997, pp. 352–355.

* cited by examiner

Primary Examiner—Maureen M. Wallenhorst
(74) Attorney, Agent, or Firm—Hardaway/Mann IP Group

(57) ABSTRACT

A method for the determination of total organic carbon in an aqueous sample by trapping the organic matter on a sorbent which is carbon free and analyzing the sorbent by combustion and determination of total $CO_2$ by IR.

4 Claims, 2 Drawing Sheets

SCHEMATIC OF SEQUENCE OF STEPS

SCHEMATIC 7
METHOD OF SAMPLE COLLECTION

SYRINGE →

CARTRIDGE →

BEAKER →

SCHEMATIC OF SEQUENCE OF STEPS ized methods for determination of TOC
LOW LEVEL TOC MEASUREMENT METHOD This United States Government has rights in this invention pursuant to contract No. DE-AC09-96-SR-18500 between the Department of Energy and Westinghouse Savannah River Company.

BACKGROUND OF THE INVENTION

1. Field of the Invention

This invention relates to methods for sampling and determining the Total Organize Carbon is an aqueous liquid.

2. Background and Prior Art

Total Organic Carbon (TOC) measurements are not new in analytical chemistry. The methods have not been developed to the extent that analyte-specific methods have been because TOC is less glamorous and typically less useful. TOC is becoming more important as regulatory focuses change and limits of detection are lowered. TOC is the method of choice for determining the purity of water in the pharmaceutical industry and for analysis of drinking water. It is increasingly recognized as a preferred method for characterizing discharges from water treatment facilities. In each case, specific target species may be present at below detectable limits but total organics are measurable and give a good measure of overall contamination. This is especially the case when the sources(s) and identities of the carbon are known.

In addition to drinking water safety and pharmaceutical safety, ultrapure water is required in many industries including semiconductor fabrication.

The TOC measurement methods all require the steps of sample collection, sample volume reduction (concentration), sample oxidation and measurement of the common oxidation product (usually $CO_2$).

Samples are obtained in bulk—the so-called grab sample—from an environmental source, from a pipeline or from a packaged sample such as water for injection. The concentration of analyte may be extremely low and volume reduction is required.

Volume reduction has historically been done by some form of distillation. The exact process is complicated by the presence of purgeable organics (VOC's) is many samples. U.S. Pat. No. 3,859,209 to Jahnsen et al. discloses a method for separating organics from a large volume of solvent and loading onto a GC column by a form of flash evaporation. U.S. Pat. No. 4,180.389 to Paul describes a process whereby the sample is purified by a form of repetitive purge and trap steps.

U.S. Pat. No. 5,401,468 to Parashnick et al. is directed to a method for the determination of total carbon in the exhaust from a diesel engine using a closed loop and a ceramic trap. No provision is made to separate organic from inorganic carbon.

U.S. Pat. No. 5,425,919 to Inone et al. describes a TOC analyzer which uses an absorbing agent containing $Ba(OH)_2$ to separate and quantify purgeable organic carbon in a TOC determination.

U.S. Pat. No. 5,574,230 to Baugh discloses an air sampling tube containing silica gel, Tenax and activated carbon for introduction by thermal desorption into a GC/MS.

The oxidation to $CO_2$ may be effected in a variety of ways. U.S. Pat. No. 4,619,902 to Bernard discloses an improved wet digestion method using persulfate and a variety of catalysts. U.S. Pat. Nos. 5,292,666 and 5,340,542 to Fabinski et al. disclose methods for determination of TOC and total nitrogen in water using thermal reactors and non-dispersive infrared gas analyzers.

U.S. Pat. No. 5,315,885 to Szinyei describes one method for quantitatively introducing a sample into a pyrolysis furnace. U.S. Pat. No. 5,567,388 to Morita et al. discloses a method for returning purgeables to the "organic side" of a semipermeable membrane after separation of inorganic carbon prior to pyrolysis.

Godec et al., U.S. Pat. No. 5,750,073 discloses a third method for conversion to $CO_2$ and measurement, viz oxidation using short wavelength UV lights and measurement of total carbon electrochemically based on breakdown products.

The sensitivity of the prior art methods of TOC analysis depends upon the sensitivity of the detection method. There remains a need for a method for concentrating the sample to effect lower detection limits which does not risk loss of purgeable organics and which minimizes handling losses between sampling and detection.

SUMMARY OF THE INVENTION

It is an object of this invention to provide a method for collection of total organic components from an aqueous sample. It is a further object of this invention to provide a method for collection which allows for the sampling of large volumes of water without loss of sampled components during handling. It is yet a further object of this invention to enable collection of a concentrated sample at a location remote from the analysis site.

It is an object of this invention to provide a method for sample collection using an apparatus which can be introduced directly or with minimal handling into the sampling port of an analytical instrument such as a furnace.

These and other objects of this invention may be met by collecting total organic carbon on passage of the medium containing the target materials to be analyzed through a column, tube or cartridge containing an inorganic, carbon-free sorbent. The sorbent may then be introduced into a furnace either with or without removal from the column, tube or cartridge.

DETAILED DESCRIPTION OF THE INVENTION

Figure 1:
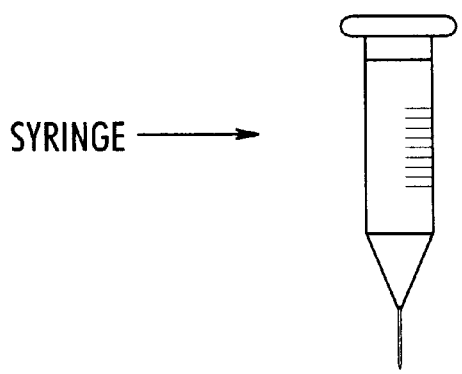
FIG. 1 is a schematic drawing showing the method of sample collection according to one embodiment of this invention.
Figure 1:
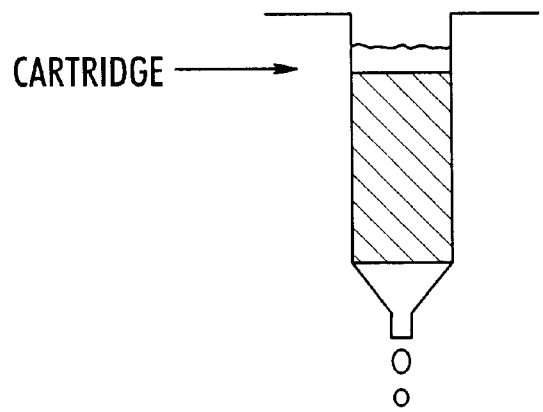
Figure 1:
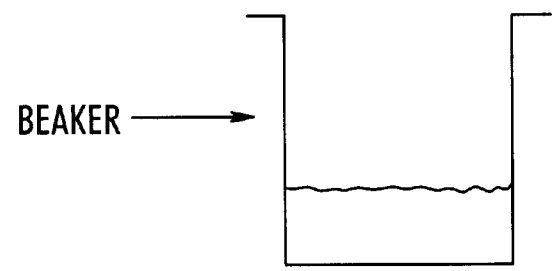
Figure 2:
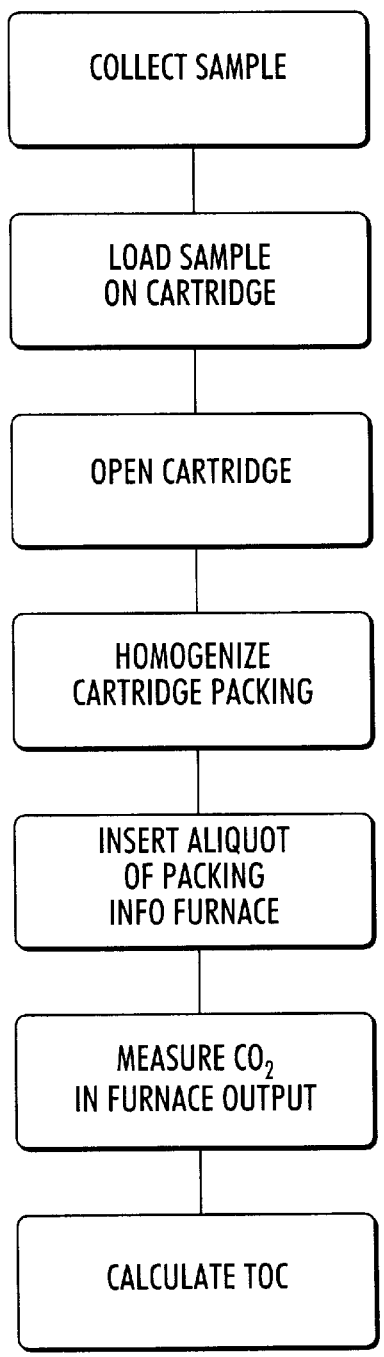
FIG. 2 is a schematic drawing showing the sequence of steps in the detection of the collected sample.

The sampling cartridge according to this invention may be made from any solid material from which carbon cannot be leached by an aqueous sample. Metals are suitable but must be thoroughly acid washed. Plastics are not preferred due to the presence of unreacted monomers and catalyst residues. Quartz and borosilicate glasses are preferred because of transparency and ease of cleaning. The tube portion may have an inner diameter of approximately 1 cm. Total length is not critical provided that space is allowed for a head of sample. A commercially available glass extraction tube or syringe may be used or the cartridge may be fabricated from borosilicate glass.

The packing material may be any granular component which when made or after suitable treatment contains no carbon. Examples include silica gel, alumina and magnesium silicate. Particle sizes may range from 10–50 mm.

The sampling cartridge may be used in any orientation provided that the effective head of the sample source is above the effective head of the receiver and that some means can be used to measure accurately the volume of liquid which has been sampled. In most applications, the cartridge is mounted vertically and loaded from the top.

As with any liquid chromatographic procedure, it is preferred to run a small volume of the sample medium (ultrapure water) through the column before introducing the sample. Sample treatment to absorb the organics is normally performed at room temperature (ca 20°C.). When the aqueous sample is hotter or colder that the packing, the sample should be allowed to equilibrate before being introduced into the sampling cartridge.

A measured volume is loaded onto the column in one or more aliquots and allowed to run through the column until the top surface is visibly dry. Alternatively, the sample may be chased using a small volume of ultrapure water.

When collection is complete on the packing, the packing is removed from the cartridge for insertion into a furnace. The packing may be removed in any of a number of ways. If the packing is located in a glass tube with integral inlet and outlet, the tube may be scored and broken to remove the segment containing the packing. If the segment containing the packing has been clamped to inlet and outlet portions, the clamps may be undone and the packing segment removed. In the preferred embodiment, the packing material is homogenized thoroughly and a measured portion is introduced into the furnace using a platinum boat. It is critical that extreme care be taken to avoid contamination during transfer. If a Class 1000 or better room is not available, manipulations should be done in a protective enclosure such as a clean air bench.

A commercially available furnace coupled to an infrared spectrometer is used to measure total $CO_2$ derived from the organic compounds trapped on the cartridge packing. One Example of a suitable instrument is a TECHMAR DOHRMAN Model DC-190/DC-183 TOC system. The analysis is performed according to the manufacturer's directions. When the sample is suspected to contain inorganic carbon, an aliquot of the homogenized sample should be shaken with a mineral acid to evolve dissolved carbonates before introduction into the furnace.

The method may be demonstrated by the following examples which are not limitative of the described invention.

EXAMPLE 1

Filter cartridges packed with 5 grams of silica gel were purchased from a commercial source (SUPELCO).

A 10 ppb organic carbon solution was prepared by diluting a 1000 ppm standard solution (Ricca Chemical Co., NIST traceable) in 18 megaohm to obtain a 10 ppb solution. One hundred ml of the diluted solution were passed through each of 5 cartridges.

After the sample had been run, the packing in each cartridge was removed and carefully mixed and 50 mg. from each was introduced using a platinum boat into a TECHMAR DOHRMAN DC-183 furnace at 800°C. The evolved $CO_2$ was measured using a TECHMAR DOHRMAN IR detector and corrected for dilution. The results are shown in Table 1.

TABLE 1

| RUN | TOC INDICATED | TOC CALCULATED |
|-----|---------------|----------------|
| 1 | 195 ugC | 9.4 ppb |
| 2 | 180 | 9.0 |
| 3 | 165 | 8.0 |
| 4 | 200 | 10.0 |
| 5 | 210 | 10.0 |
| 6 | 193 | 9.5 |

It is apparent from the description above that the invention provides a method for the determination of TOC which is applicable to a high degree of accuracy because of the large volume of sample which may be concentrated quickly and efficiently. It is apparent also that the sampling may be performed simply and with a minimum a mount of manipulation. Modifications in the details of the description which are apparent to one skilled in the art are included in the scope of the invention.

I claim:

1. A method for the determination of total organic carbon in an aqueous sample comprising:

a) preparing a sampling cartridge comprising a solid sorbent for organic carbon compounds in a tubular container;

b) passing a measured volume of the aqueous sample through the cartridge so that organic compounds in the sample adsorb onto the solid sorbent;

c) removing said sorbent from said cartridge and mixing said sorbent thoroughly to effect complete homogenation of the sorbent containing adsorbed organic carbon compounds;

d) introducing a measured portion of said homogenized sorbent into a furnace;

e) subjecting said homogenized sorbent to a combustion reaction in the furnace to produce carbon dioxide from the organic carbon compounds adsorbed onto the sorbent, and measuring the carbon dioxide produced by the use of an infrared detector; and f) calculating the carbon total organic of said aqueous sample from the amount of carbon dioxide measured.

2. A method according to claim 1, wherein said solid sorbent is silica gel.

3. A method according to claim 1, wherein said solid sorbent in alumina.

4. A method according to claim 1 wherein said solid sorbent is magnesium silicate.

* * * * *